United States Patent
Bulard et al.

(10) Patent No.: US 6,716,030 B1
(45) Date of Patent: Apr. 6, 2004

(54) UNIVERSAL O-BALL MINI-IMPLANT, UNIVERSAL KEEPER CAP AND METHOD OF USE

(75) Inventors: Ronald A. Bulard, Ardmore, OK (US); Victor I. Sendax, New York, NY (US); Stephen J. Hadwin, Ardmore, OK (US)

(73) Assignee: IMTEC Corporation, Ardmore, OK (US)

( * ) Notice: Subject to any disclaimer, the term of this patent is extended or adjusted under 35 U.S.C. 154(b) by 0 days.

(21) Appl. No.: 10/031,256
(22) PCT Filed: Apr. 21, 2000
(86) PCT No.: PCT/US00/10827
§ 371 (c)(1),
(2), (4) Date: Jul. 15, 2002
(87) PCT Pub. No.: WO00/64369
PCT Pub. Date: Nov. 2, 2000

Related U.S. Application Data

(60) Provisional application No. 60/130,684, filed on Apr. 23, 1999.

(51) Int. Cl.$^7$ .................................................. A61C 8/00
(52) U.S. Cl. ...................................................... 433/174
(58) Field of Search ................................ 433/174, 173, 433/172, 170, 169, 176, 221

(56) References Cited

U.S. PATENT DOCUMENTS

| 4,193,194 A | | 3/1980 | Dalise | |
|---|---|---|---|---|
| 4,713,003 A | * | 12/1987 | Symington et al. | 433/173 |
| 5,049,072 A | * | 9/1991 | Lueschen | 433/173 |
| 5,061,181 A | * | 10/1991 | Niznick | 433/174 |
| 5,098,295 A | * | 3/1992 | Durr et al. | 433/172 |
| 5,211,561 A | * | 5/1993 | Graub | 433/169 |
| 5,520,540 A | * | 5/1996 | Nardi et al. | 433/172 |
| 5,639,237 A | * | 6/1997 | Fontenot | 433/173 |
| 5,749,732 A | | 5/1998 | Sendax | |
| 5,842,864 A | * | 12/1998 | Unger | 433/172 |

* cited by examiner

*Primary Examiner*—John J. Wilson
*Assistant Examiner*—Melba Bumgarner
(74) *Attorney, Agent, or Firm*—Norris McLaughlin & Marcus

(57) ABSTRACT

The present invention relates to a one-piece dental implant having a threaded shaft which is tapered on one end and has a non-circular abutment on the other end, and a ball-shaped head mounted on said non-circular abutment. The inventive dental implants are advantageous in that they are of one-piece design, and, therefore, do not have multiple parts which can loosen over time. The present invention further relates to a keeper cap for use with the inventive dental implants, which is adapted to retain either O-ring-shaped inserts or plastic inserts. The inserts can be switched easily at any time without the need to remove the keeper cap from the denture or to form a new denture around new caps. The inventive dental implant and keeper cap make up a kit along with the O-ring-shaped inserts and the plastic inserts, which kit is useful in connection with the formation of fixed or removable prostheses.

10 Claims, 5 Drawing Sheets

FIG.5
FIG.6
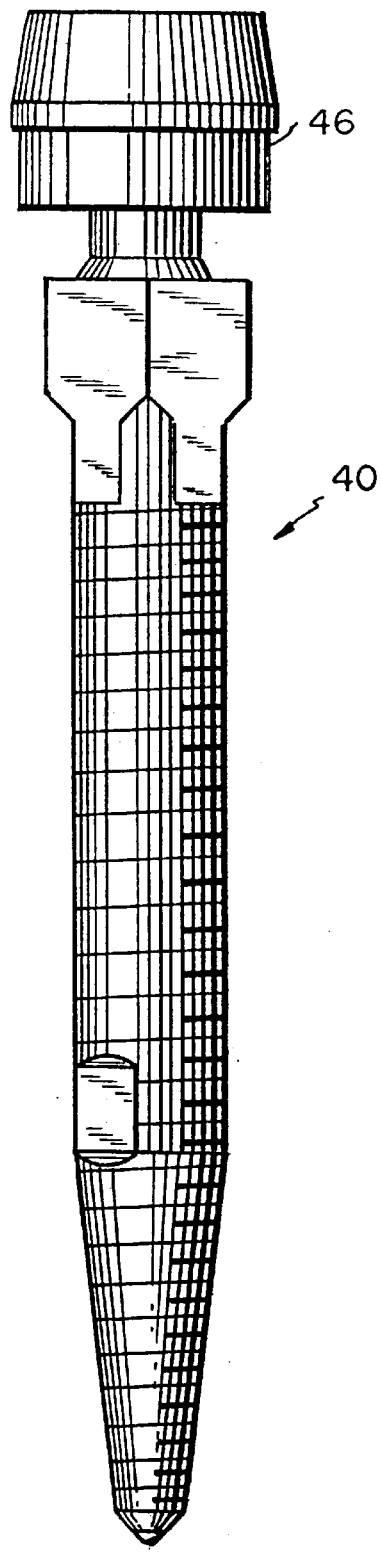
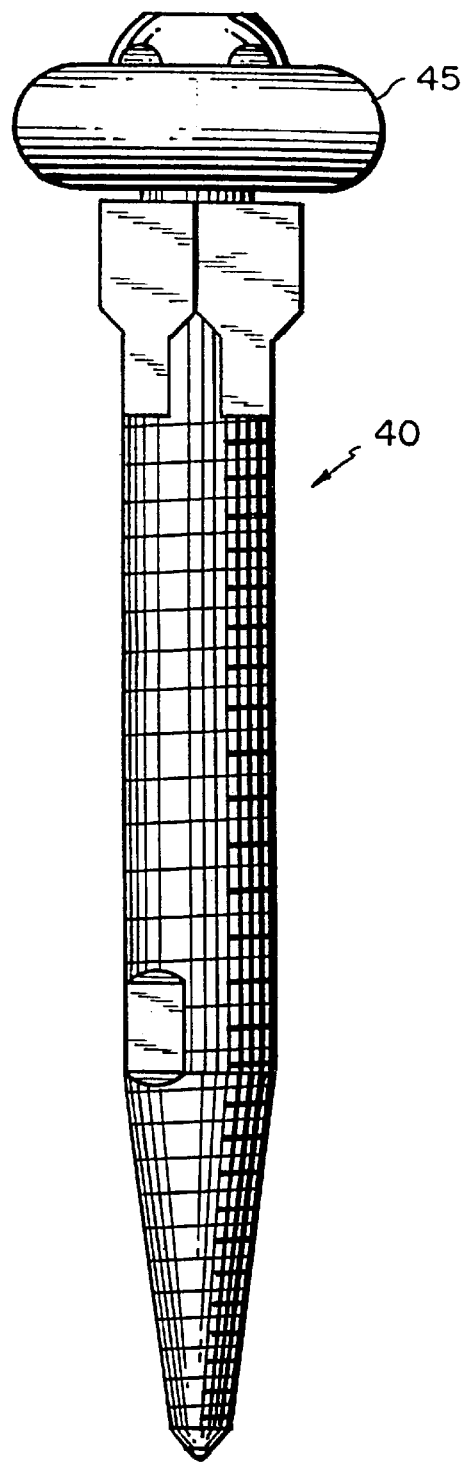

FIG.7
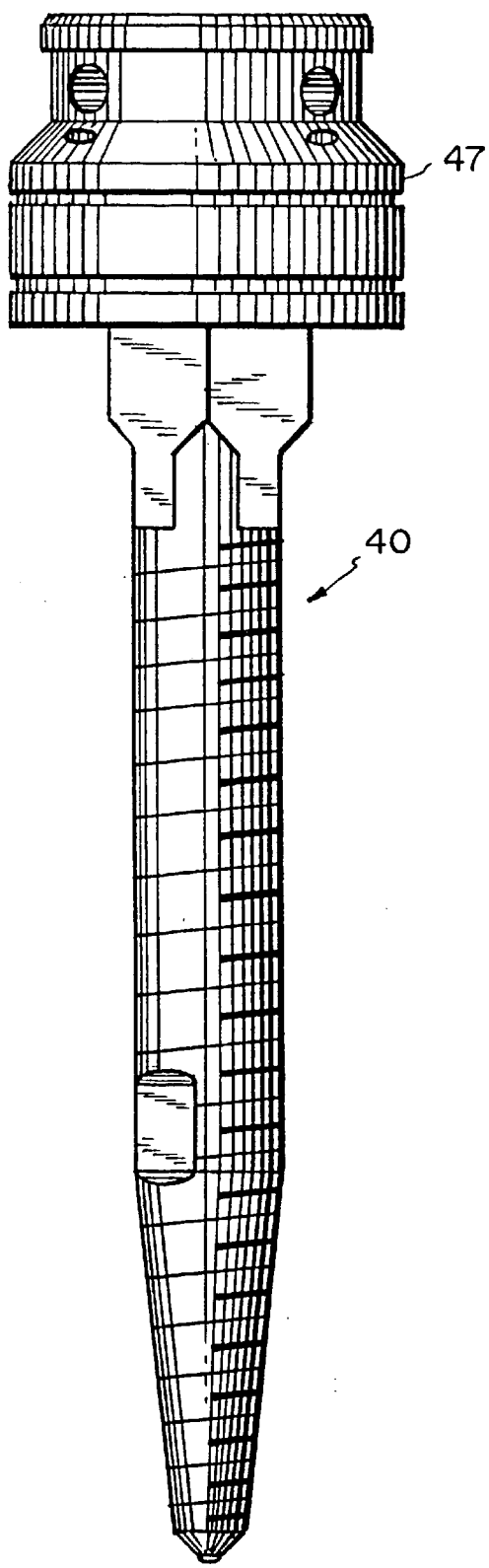
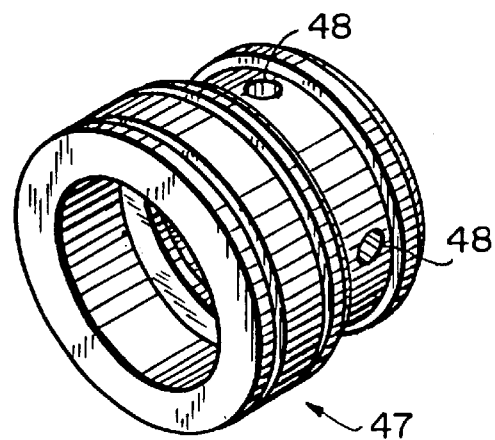
FIG.8

UNIVERSAL O-BALL MINI-IMPLANT, UNIVERSAL KEEPER CAP AND METHOD OF USE

This application is a 371 of PCT/US00/10827, on Apr. 21, 2000.

This Application claims the benbfit of Provisional Application Ser. No. 60/130,684 filed Apr. 23, 1999.

BACKGROUND OF THE INVENTION

1. Field of the Invention

The present invention relates to an improved O-ball dental implant, to an improved keeper cap, and to the use of the improved implant and keeper cap for fixed or removable prosthetic applications.

2. Description of Related Art

The use of combinations of O-ring abutments and standard dental implants is well known in the art. Previously, these have not been integrated into a single device. Instead, the conventional practice has been to set one or more standard dental implant bodies, i.e., without the O-ring abutments. Thereafter, the O-ring abutments have been mounted onto the dental implant bodies, generally by screwing the O-ring abutment into the implant bodies. Then, fixed or removable prostheses have been mounted onto the combinations of the O-ring abutments and the dental implant bodies according to a variety of procedures well known in the art.

A problem with these types of fixtures is that the connections between the O-ring abutments and the dental implant bodies can loosen over time. Another problem is that these types of fixtures exhibit bacteria and ionic microleakage at the joints. It would be beneficial to have the means to avoid these problems.

A third problem is that the standard implant bodies typically are large in diameter, and this causes problems in setting these implant bodies in the bone. Specifically, surgical intervention is required, which translates to multiple office visits and increased costs, which increases both the physical and financial discomfort to the patient. This problem is addressed in my earlier U.S. Pat. No. 5,749,732, which issued on May 12, 1998 (hereinafter "my earlier patent"). The contents of my earlier patent are fully incorporated herein by reference.

The solution to this third problem as outlined in my earlier patent was to provide 1) a mini-dental implant of small diameter and strong composition, such as titanium or an alloy thereof, and 2) a nonsurgical method of placing the implants comprising setting the implants directly through both gum and bone, thereby avoiding the need for surgery to incise and flap open the gum to expose the underlying bone as done previously. Because surgery was avoided, both the implants and the denture could be mounted in a single office visit, thereby reducing the cost and incidence of pain to the patient.

According to the teachings of my prior patent, the dental implant described therein comprises a non-circular abutment, preferably of square, triangular, hexagonal or any other shape that permits threaded advance of the shaft by fingers or tools. See, my prior patent at column 2, lines 58–60.

Therefore, it was an object of the present invention to overcome the problems associated with the conventional combinations of distinct O-ring abutments and dental implants, while at the same time provide advantages similar to those described in my previous patent.

Further, the use of keeper caps fitted with O-ring-shaped inserts or plastic inserts in order to removably fix a denture to an O-ring abutment is also well known. Previously, the flexibility to use either the O-ring-shaped insert or the plastic insert has not been enjoyed. Since the keeper caps are usually firmly adhered to the denture, switching from keeper caps containing O-ring-shaped inserts to those containing plastic inserts or vice versa conventionally has not been done. This is undesirable because the O-ring-shaped inserts are conventionally made of rubber, and, thus, are more gentle, and therefore have their greatest usefulness early on in the treatment when the patient's comfort level is low. However, as time passes, and the patient's comfort level rises, the use of the more rigid plastic inserts may become desirable.

Therefore, it was another object of the present invention to provide a means that would allow the practitioner to "switch" from the use of O-ring-shaped inserts to the use of plastic inserts or vice versa without having to remove the keeper cap from the denture or to form a new denture around new keeper caps.

SUMMARY OF THE INVENTION

These and other objects were met by present invention, which relates in a first embodiment to a one-piece dental implant comprising the following distinct regions:

a) a threaded shaft having first and second ends and being tapered on said first end;

b) a non-circular abutment attached to said second end of said threaded shaft; and c) a ball-shaped head attached to said non-circular abutment.

The present invention relates in a second embodiment to a keeper cap adapted to be secured to a dental implant having a ball-shaped head via an O-ring-shaped insert or a plastic insert retained in said keeper cap, wherein said keeper cap has the structure generally of first and second joined cylinders having first and second diameters, respectively, the keeper cap is closed on one end thereof, and wherein said first diameter is selected to accept and retain said O-ring-shaped insert, and said second diameter is selected to accept and retain said plastic insert.

The present invention relates in a third embodiment to a kit comprising:

a) a one-piece dental implant comprising the following distinct regions:
  i) a threaded shaft having first and second ends and being tapered on said first end;
  ii) a non-circular abutment attached to said second end of said threaded shaft; and
  iii) a ball-shaped head attached to said non-circular abutment;

b) a keeper cap adapted to be secured to said dental implant via an O-ring-shaped insert or a plastic insert retained in said keeper cap, wherein said keeper cap has the structure generally of first and second joined cylinders having first and second diameters, respectively, the keeper cap is closed on one end thereof, and wherein said first diameter is selected to accept and retain said O-ring-shaped insert, and said second diameter is selected to accept and retain said plastic insert;

c) an O-ring-shaped insert adapted to be accepted and retained in said keeper cap and removably attached to said dental implant; and d) a plastic insert adapted to be accepted and retained in said keeper cap and removably attached to said dental implant.

The present invention relates in a fourth embodiment to a method of forming a removable prosthesis comprising:

a) providing the inventive kit;

b) inserting said dental implant into the jaw-bone of a patient;

c) forming said removable prosthesis around said keeper cap containing said O-ring-shaped insert or said plastic insert; and d) securing said removable prosthesis to the jaw-bone of the patient by attaching the keeper cap via said O-ring-shaped insert or said plastic insert to said dental implant.

Finally, the invention relates in a fifth embodiment to a method of forming a fixed prosthesis onto a combination of an O-ring abutment screwed into a dental implant body, wherein the improvement comprises forming the fixed prosthesis onto the inventive one-piece dental implant.

BRIEF DESCRIPTION OF THE DRAWINGS

The invention will now be described in greater detail with reference to the drawings, wherein:

FIG. 5 is a lengthwise view of the inventive dental implant with mounted plastic insert.

FIG. 6 is a lengthwise view of the inventive dental implant with mounted O-ring-shaped insert.

FIG. 7 is a lengthwise view of the inventive dental implant with the inventive keeper cap mounted over the plastic insert (not shown) or O-ring-shaped insert (also not shown).

FIG. 8 is a perspective of the inventive keeper cap.

DETAILED DESCRIPTION OF THE INVENTION

Figure 1:
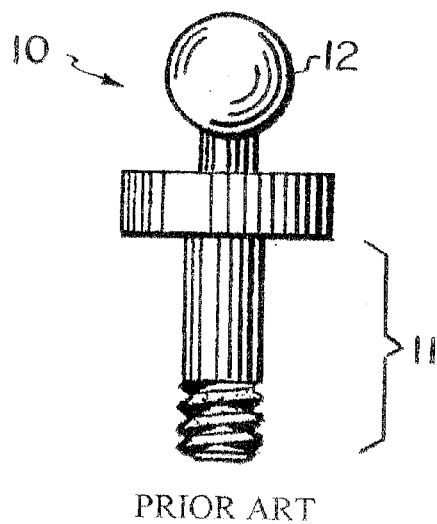
FIG. 1 is lengthwise view of a conventional O-ring abutment to be screwed into a conventional implant body (not shown).
Figure 2:
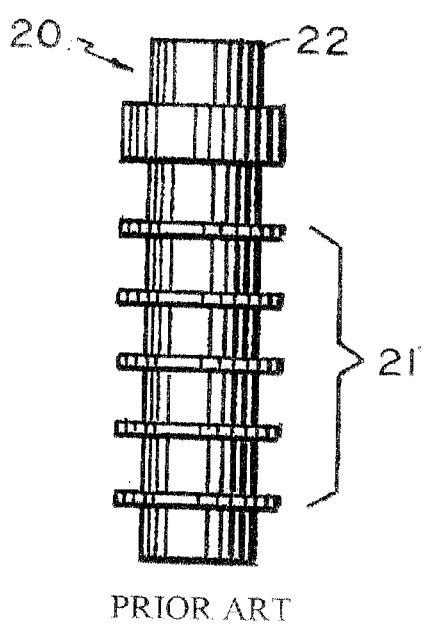
FIG. 2 is a lengthwise view of a conventional implant body, into which a conventional O-ring abutment (not shown) is screwed.
Figure 3:
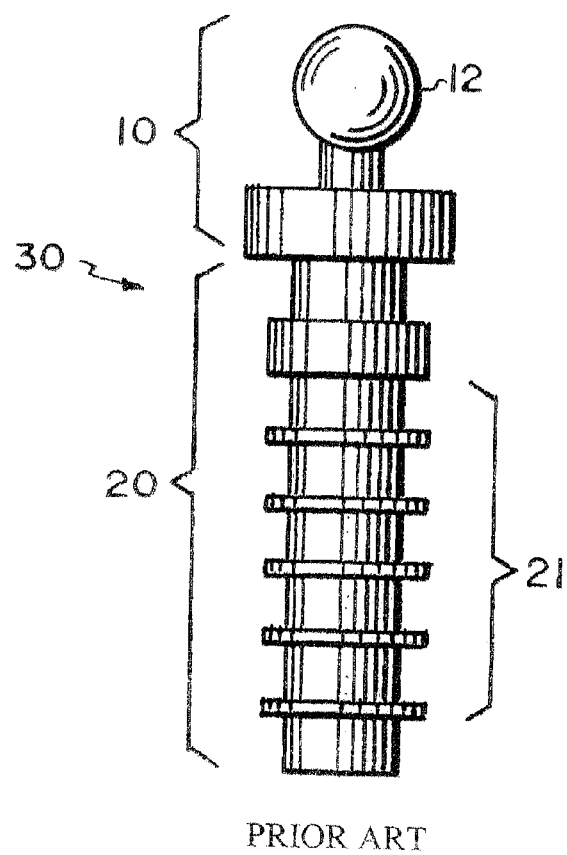
FIG. 3 is a lengthwise view of a conventional O-ring abutment screwed into a conventional implant body.

As previously discussed, the prior art made use of multiple-piece units for supporting fixed and removable prosthetic applications. Referring to FIG. 1, a first component was conventionally an O-ring abutment 10 comprising a threaded shaft 11 and ball-shaped head 12. Referring to FIG. 2, a second component was conventionally an implant body 20 comprising a threaded shaft 21 and an opening in head 22, which cooperated with and accepted the threaded shaft of O-ring abutment 10. In practice, O-ring abutment 10 was screwed into implant body 20 to yield the construct 30 shown in FIG. 3. Since the construct shown in FIG. 3 comprised multiple parts, the bond between the component parts could loosen over time, which could be problematic.

Figure 4:
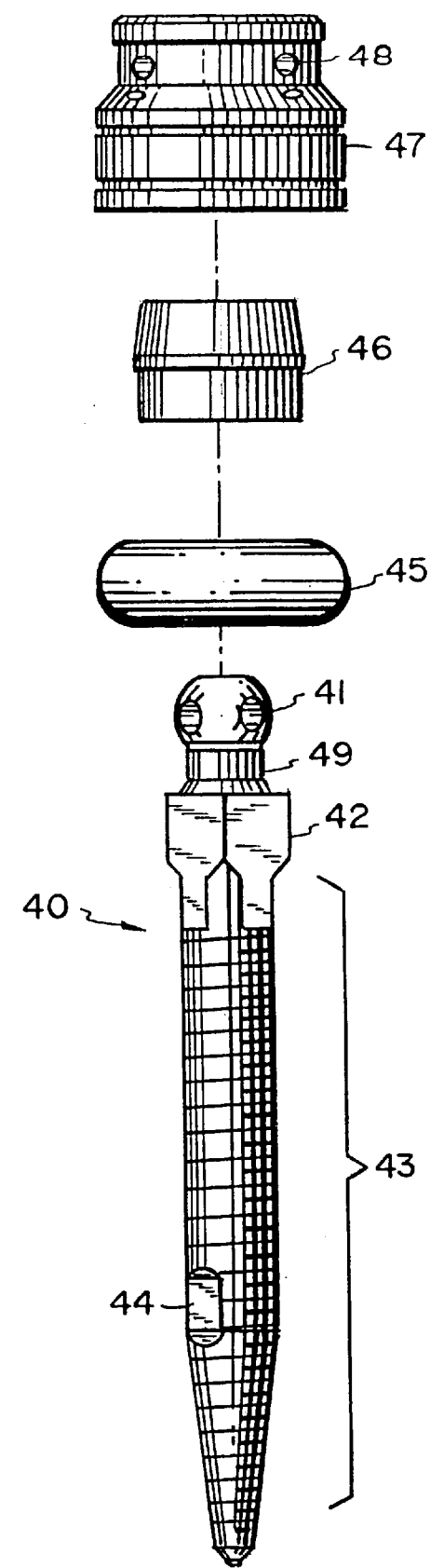
FIG. 4 is a lengthwise view of the various components of the present invention.
Figure 9:
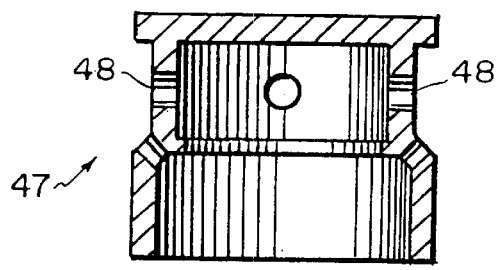
FIG. 9 is a cross-section of the inventive keeper cap.

Referring to FIG. 4, the present invention solves this problem by fully integrating the O-ring abutment and the implant body. Thus, as shown in FIG. 4, the present invention relates in a first embodiment to a one-piece dental implant 40 which comprises distinct but integrated ball-shaped head 41, non-circular abutment 42, and threaded shaft 43.

Generally, the inventive dental implant ranges in overall length from about 15 to about 25 mm, preferably from about 17 to about 22 mm.

Figure 10A:
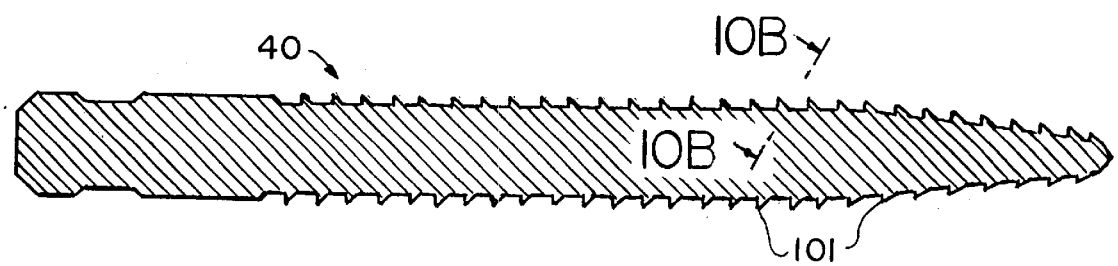
FIG. 10 is a lengthwise view of the inventive dental implant showing an exemplary thread design, which is highlighted in Detail B at a scale of 24:1, and shows a distance of 0.020 inches between threads.
Figure 10B:
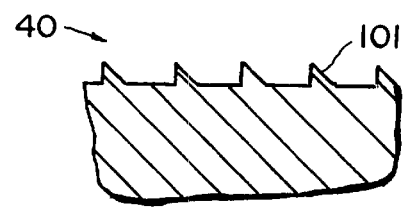

The threaded shaft comprises a tapered end, and ranges in diameter from about 1 to about 2 mm, and preferably about 1.8 mm. The length of the threaded shaft likewise ranges from about 10 to about 19 mm, and preferably from about 12 to about 17 mm. The thread design and positioning on the threaded shaft can be varied over a wide range. As shown, for example, in FIG. 10, a helix of self-tapping cutting threads 101 promotes progressive draw of the inventive dental implant into dense bone. A narrow apex of crest of thread form minimizes stress from rotational forces in penetrating dense materials, and also results in minimal torque being required to advance the inventive dental implant each revolution. Moreover, a fishbone-like shape reduces the likelihood of the inventive dental implant pulling out of bone.

Further, in an especially preferred embodiment, a portion of the surface of the threaded shaft contains an anti-rotational flat 44, as shown in FIG. 4, which is not threaded to reduce any (small) likelihood of unintentional rotation (unthreading) of the dental implant from the bone in which it resides. Advantageously, the surface of the threaded shaft at a location beginning between about 4 to about 8 mm, preferably about 4.6 mm, from the shaft end is provided with such a flattened, unthreaded area, the area of which in cross-section defines a minor chord of a circle. The length of the flat in the longitudinal direction of the threaded shaft ranges in length from about 1 to about 5 mm, and is preferably about 1 mm.

In a preferred embodiment, the threaded shaft adjoins non-circular abutment 42, as shown in FIG. 4, which, because of its non-circular shape, can be grasped with a rachet or other tool to facilitate the insertion of the dental implant into bone. The non-circular abutment ranges in length from about 1.5 to about 4 mm, and is preferably about 2.5 mm in length. The non-circular abutment is preferably of square, triangular, hexagonal or any other shape that permits threaded advance of the threaded shaft by fingers or tools.

In a preferred embodiment, the ball-shaped head is attached to the non-circular abutment via a circular neck 49, as shown in FIG. 4, which ranges in length from about 0.5 to about 1.5 mm, and is most preferably about 0.8 mm. The diameter of the circular neck, in turn, ranges from about 0.5 to about 1.8 mm, and is preferably about 1.4 mm.

Finally, the ball-shaped head ranges in diameter from about 1 to about 2 mm, and is preferably about 1.7 mm.

The dental implant is formed of any strong metal or alloy thereof, and especially from titanium or an alloy thereof with another metal, for example, aluminum and/or vanadium. The best mode is to use a titanium alloy rod having the formula $Ti_6Al_4V$, which satisfies the American Society for Testing Materials F-136 (ASTM F-136).

Because of their small diameter compared with conventional implants, the novel implants can be placed without gum surgery. A small diameter drill is used to prepare a short cylindrical starting bore going right through the gum into the jaw bone. Because of its minute diameter there is almost no gum bleeding. As a matter of fact, the minute blood droplet on the gum serves as a marker to assist the dentist in the next step of placing the dental implant through the gum hole into the hidden-from-view jaw bone.

If desired, several drills of successively increasing diameters, but all still smaller than the dental implant diameter may be used. Other tools can be used to thread the dental implant into the jaw bone.

The implants are advantageously positioned along the apex-line for the jaw bone. While desirably parallel they might not be absolutely so but this does not pose a problem in the multiple placements and removals of the denture during fitting. Boring out the anchor holes in the denture bottom accommodates each fitting the final hardening locking the abutment heads in place.

If desired the dentist can even shape the placed abutment heads if he/she deems it advisable for parallelism.

The ultra-small width makes it uniquely possible for the inventive dental implants to be inserted directly through the soft tissue into the underlying bone without any flap surgery incisions or sutures making for a much more patient-friendly procedure than is typical of conventional implant systems.

Further the ultra-slim width permits a minimal encroachment on usually sparse amounts of good quality tough epithelialized gum tissue making it all the more likely that the dental implant will be more comfortable not only at time of placement but during the aftercare period and beyond.

Thus, the inventive dental implants can be placed using the same nonsurgical method as described in my prior patent, and all pertinent details are fully incorporated herein by reference.

Because the inventive dental implants have a one-piece design, they are not susceptible to the microleakage problems on the bacteria and ionic levels, which were characteristic of the prior art multiple-piece designs. Accordingly, the inventive dental implants are less likely to be rejected by the patient, less likely to lead to infection, and less likely to corrode.

Once the inventive dental implants have been positioned, they can be used for both fixed and removable prosthetic applications. The details of these procedures are well known to persons having ordinary skill in the art, and, therefore, these well known details are not repeated here. See, for example, Michael S. Block et al., *Implants in Dentistry*, W. B. Saunders Company, Philadelphia, Pa., 1997, the entire contents of which are incorporated herein by reference.

However, referring to FIGS. 5–9, in an especially preferred embodiment, use is made of the inventive keeper cap 47 to mount a removable prosthesis, for example, a denture (not shown), to the ball-shaped head region (not shown) of dental implant 40. The keeper cap, as discussed above, is adapted to accept and retain either O-ring-shaped insert 45 or plastic insert 46, which, in turn, removably attaches to the ball-shaped head of dental implant 40. The keeper cap 47 can be made of any conventional material, and is preferably made from the same material as the dental implant, i.e., titanium or from an alloy of titanium with another metal, for example, aluminum and/or vanadium. The best mode is to use a titanium alloy rod having the formula $Ti_6Al_4V$, which satisfies ASTM F-136. Once the prosthetic attachment cap is mounted, the prosthesis can be formed in the conventional manner.

In a preferred embodiment, the keeper cap has an interior diameter in the portion that accepts and retains the O-shaped ring insert of from about 2 to about 6 mm, and is preferably about 4.5 mm in interior diameter. The interior diameter of the portion that accepts and retains the plastic insert ranges from about 2 to about 4 mm, and is preferably about 3.1 mm in interior diameter.

In an especially preferred embodiment, the portion of the keeper cap that accepts and retains the plastic insert is fitted with one or more dimples 48, as shown, for example, in FIG. 8. These dimples serve two primary functions. First, they prevent the rotation of the keeper cap in the prosthesis once the acrylic plastic is set. Second, their presence compresses the wall of the keeper cap at that location, and this allows the plastic insert to snap into place.

An advantage of the inventive keeper cap is that its use permits the switching from O-ring inserts or plastic inserts. To remove a plastic insert from the keeper cap, a reaming instrument is used to thin out or ream out the inner wall of the plastic insert sufficiently so it is thin enough to deform by cutting or pressing it centrally until it crumples and can be readily excavated out of the keeper cap. To install a plastic insert, the plastic insert is pressed into the keeper cap until it snaps into place, partially aided internally by the presence of the little dimples on the inner wall of the keeper cap.

Instead of using the inventive keeper cap, it is also possible to use conventional keeper caps having either O-ring-shaped inserts or plastic inserts or other inserts, for example, nylon inserts. Again, once the prosthetic attachment cap is mounted, the prosthesis can be formed in the conventional manner.

Alternatively, it is possible to place a shim, or tubular spacer, around the dental implant prior to mounting the prosthesis so as to facilitate the removal of the prosthesis later. This can be particularly useful where the prosthesis is built up over several office visits.

The following non-limiting exemplary protocol illustrates practice of the present invention:

EXAMPLE

1. Jaw Anatomy Evaluation

The clinician should palpate the labio-lingual or bucco-lingual width dimensions to estimate the optimal direction and angulation for exploratory drill entry through crestal soft tissue then through the cortical bone layer and finally, four to five millimeters into the underlying medullary bone. Bone calipers may also be used to estimate actual bony width, once crestal soft tissue anesthesia is obtained. A point probe may also be used to advantage in estimating soft tissue depth and quality of the underlying bone.

2. Drill Specifications

An appropriate drill may be a tapered 700 Xl or 700 XXl 1010 or 1012 carbide fissure bur or tapered diamond drill (coarse grain is preferable) used in a friction grip-water-cooled air turbine handpiece. This precision tool is carefully speed controlled by a foot rheostat to provide adequate torque while achieving minimal heat production.

3. Drill Technique

The required drilling is really a micro-addition in comparison to larger scale drilling operations for conventional implants. The primary idea here is to ignore the concept of a precise osteotomy and think of the site procedure as comparable to developing a minimal "starter" hole.

4. Placement of Dental Implants

The placement of a dental implant into the pilot opening through overlying attached gingiva on the ridge crest is facilitated using a small implant carrier device and then using the same device to initiate the self-tapping process by turning the carrier clockwise between thumb and index finger while exerting downward pressure on the abutment held in the long axis of the implant. This process provides the initial "take" into bone of the threaded portion of the implant body, and is enhanced by the presence of the small "flat" without threads, which is advantageously located about one-third the distance from the apex of the implant, which permits any small bony particle accumulation to build up in the area of the "flat" helping to avoid a significant interference with the ongoing insertion process, and with time in situ, acting also as an autogenous bone graft focus, or stop which when fully calcified functions as an implant anti-rotation barrier, reducing the likelihood that any istrogenic counterclockwise moments of force could work negatively to back out the implant. This anti-rotation feature is probably not critical to routine success of a dental implant but is added insurance especially for longer-term applications.

A winged thumb screw or analogous tool is used to continue the implant insertion process as soon as noticeable bony resistance is experienced and a more efficient tool is indicated. The wings of this device permit more thumb and finger purchase and control than the carrier tool. The thumb screw is kept in play until once again obvious resistance is encountered during the insertion process.

Ratchet and abutment head adapter tools are next utilized for the final stage of implant insertion, where carefully controlled, small incremental ratchet turns will provide efficient self-tapping in everything except the very densest of bone and assurance that the implant will demonstrate a rocklike integration with the bone that can then indeed be immediately loaded for functionability. For extremely dense bone sites experienced at deep levels it may be preferable not to try and force the insertion process, but rather to reverse the ratchet and back out the implant. It is then entirely possible to drill through the dense bone. The implant may then be reintroduced into the self-tapped site with carrier and thumb screw devices until once again resistance is met, at which point the ratchet and adapter are again employed to finalized the seating of the implant up to its abutment head protruding from the gingival soft tissue at its full length but with no neck or thread portions visible ideally.

5. Reconstruction

The reconstructive protocol is based on three elements: (a) The universal O-ball abutment functions as an all-purpose abutment for both removable and fixed applications (and for both transitional and long-term applications), permitting for the first time in implant prosthodontics a single one piece implant to provide this range of options. (b) The Elastomeric Shim (or spacer) eliminates angulation problems from both transitional and long term applications (and simplifies the complete lab process.) (c) The "Ponabut" design for fixed prosthetic applications (both transitional and long-term) provides maximum aesthetic, phonetic and hygienic design options.

Additionally, for transitional applications, a reinforcement system, utilizing either intertwined (paired) stainless steel ligature twists, or IMTEC Titanium Mesh strips, or a combination of the two, is recommended to provide additional strength for such transitional prosthodontics cases, with particular benefits demonstrable for close bite problem situations.

If a removable application is called for by the treatment plan the O-ball design can provide support for a transitional removable full or partial denture including the overdenture type. The attachments can be either the O-ring type for slightly less forceful gripping of the abutment head or the plastic type cap which has a somewhat more positive retentive grip while still providing some rotational compliance. The most forgiving attachment is the O-ring type and is probably the attachment of choice if there is any doubt at the outset as to the degree of bony integration upon insertion of the dental implant. Graduating from O-Ring to plastic attachment is entirely possible as a routine progression where indicated by the need for more positive retentive force, since the total replacement of one attachment for another is a matter of a brief intraoral procedure which is readily accomplished.

Step-by-step, the intra-oral retrofit of any removable prosthesis utilizing the O-ball abutment and keeper cap with either an O-ring attachment or plastic attachment, is as follows. Transfer the head position of the abutment(s) to the removable prosthesis tissue bearing undersurface. Using an acrylic laboratory carbide or equivalent instrument, excavate out the area of the abutments. Lubricate the abutment head(s) with a thin Vaseline coating, place an elastomeric shims (spacer) over the cervical half of the abutment while permitting the O-ball half of the abutment to protrude uncovered. As an additional protective option, place a small circle of latex rubber (punched out in the center with the smallest rubber dam hole) over the O-ball head until it rests on the lower half of the abutment shoulder which is prevented from further cervical progression by the presence of the elastomeric shim (or spacer). The keeper cap with rubber O-ring inserted, or with plastic insert, are then placed over the O-Ball until fully seated and tested for easy rotational compliance. Refit the removable denture with the relieved openings over the attachments to test again for adequate passivity and clearance, and insert over the attachments intraorally, instructing the patient to close gently but firmly into centric occlusion, and allowing acrylic resin to fully cure and hard set.

The above technique is essentially the same for producing either transitional or longer-term fixed prosthodontics. Preferably, an elastomeric shim is slipped over the abutment prior to waxing up for a casting or overlaying to produce an acrylic restoration.

It will be understood that the specification and examples are illustrative but not limitative of the present invention and that other embodiments within the spirit and scope of the invention will suggest themselves to those skilled in the art.

What is claimed is:

1. A one-piece dental implant for placement into bone, said one-piece dental implant extending between a first end and a second end, and said one-piece dental implant comprising the following distinct regions formed into one piece:
   a) a threaded shaft tapering to a point at said first end;
   b) a ball-shaped head at said second end; and
   c) a non-circular abutment positioned between said threaded shaft and said ball-shaped head.

2. The one-piece dental implant according to claim 1, wherein:
   the one-piece dental implant ranges in overall length from about 17 to about 22 mm;
   the threaded shaft ranges in length from about 12 to about 17 mm, and has a maximum diameter along its length of about 1.8 mm;
   a circular neck is positioned between the ball-shaped head and the non-circular abutment, and the circular neck has a length of about 0.8 mm and a diameter of about 1.4 mm; and
   the ball-shaped head has a diameter of about 1.7 mm.

3. The one-piece dental implant according to claim 1, wherein the threaded shaft is not threaded along a portion of its surface.

4. The one-piece dental implant according to claim 1, which is formed of titanium or of an alloy of titanium with another metal.

5. A kit comprising:
   a) the one-piece dental implant according to claim 1;
   b) a keeper cap adapted to be secured to said dental implant via an O-ring-shaped insert or a plastic insert retained in said keeper cap, wherein said keeper cap has the structure generally of first and second joined cylinders having first and second diameters, respectively, the keeper cap is closed on one end thereof, and wherein said first diameter is selected to accept and retain said O-ring-shaped insert, and said second diameter is selected to accept and retain said plastic insert;
   c) an O-ring-shaped insert adapted to be accepted and retained in said keeper cap and removably attached to said dental implant; and
   d) a plastic insert adapted to be accepted and retained in said keeper cap and removably attached to said dental implant.

6. A method of forming a removable prosthesis comprising:
   a) providing the kit according to claim 5;
   b) inserting said dental implant into the jaw-bone of a patient;
   c) forming said removable prosthesis around said keeper cap containing said O-ring-shaped insert or said plastic insert; and
   d) securing said removable prosthesis to the jaw-bone of the patient by attaching the keeper cap via said O-ring-shaped insert or said plastic insert to said dental implant.

7. A method of forming a fixed prosthesis, said method comprising forming the fixed prosthesis onto the dental implant according to claim 1.

8. A non-surgical method of placing a dental implant, said method comprising:
   a) providing the dental implant according to claim 1;
   b) providing a starting bore through a patient's gum into said patient's jaw bone; and
   c) threading said dental implant through said starting bore into said patient's jaw bone.

9. A one-piece dental implant for placement into bone, said one-piece dental implant extending between a first end and a second end, and said one-piece dental implant comprising the following distinct regions formed into one piece:
   a) a threaded shaft tapering to a point at said first end;
   b) a ball-shaped head at said second end; and
   c) a ratchet-engaging portion positioned between said threaded shaft and said ball-shaped head;
      wherein said ball-shaped head is of a size and is positioned above said ratchet-engaging portion in such a way that said ratchet-engaging portion can be engaged with a ratchet from above said ball-shaped head.

10. A combination comprising:
    a) a dental implant according to claim 1; and
    b) a plastic insert or an O-ring applied to the ball-shaped head of said dental implant.

* * * * *